United States Patent [19]

Razdan et al.

[11] 3,934,024
[45] Jan. 20, 1976

[54] METHOD OF PRODUCING ANALGESIA AND COMPOSITIONS USEFUL THEREIN

[75] Inventors: Raj Kumar Razdan, Belmont; Harry George Pars, Lexington, both of Mass.

[73] Assignee: Sharps Associates, Cambridge, Mass.

[22] Filed: Feb. 18, 1975

[21] Appl. No.: 550,286

Related U.S. Application Data

[63] Continuation-in-part of Ser. No. 210,170, Dec. 20, 1971, Pat. No. 3,883,551, which is a continuation-in-part of Ser. No. 852,928, Aug. 25, 1969, abandoned.

[52] U.S. Cl. .................................................. 424/275
[51] Int. Cl.$^2$ .......................................... A61K 31/38
[58] Field of Search ..................................... 424/275

[56] References Cited

UNITED STATES PATENTS

| | | | |
|---|---|---|---|
| 3,462,458 | 8/1969 | McIntyre | 260/343.2 |
| 3,467,675 | 9/1969 | Peterson et al. | 260/343.2 |

FOREIGN PATENTS OR APPLICATIONS

| | | | |
|---|---|---|---|
| 2,041,610 | 3/1971 | Germany | 260/327 |

*Primary Examiner*—Stanley J. Friedman
*Attorney, Agent, or Firm*—Merriam, Marshall, Shaprio & Klose

[57] ABSTRACT

A method of relieving pain in a mammalian patient suffering therefrom by administering 1,2-dihydro-5,5-dimethyl-10-hydroxy-8-(3-methyl-2-octyl)-3H,5H-thiopyrano[2,3-c][1]benzopyran.

2 Claims, No Drawings

METHOD OF PRODUCING ANALGESIA AND COMPOSITIONS USEFUL THEREIN

This application is a continuation-in-part of our copending application Ser. No. 210,170 filed Dec. 20, 1971, now U.S. Pat. No. 3,883,551, which in turn is a continuation-in-part of our application Ser. No. 852,928 filed Aug. 25, 1969, now abandoned.

This invention relates to the use of 1,2-dihydro-5,5-dimethyl-10-hydroxy-8-(3-methyl-2-octyl)-3H,5H-thiopyrano[2,3-c][1]benzopyran as an analgesic agent, and to pharmaceutical compositions containing the compound.

According to the present invention it has been discovered that 1,2-dihydro-5,5-dimethyl-10-hydroxy-8-(3-methyl-2-octyl)-3H,5H-thiopyrano[2,3-c][1]benzopyran (compound I) effects analgesic activity when administered to a mammalian patient suffering from pain. Compound I has the formula

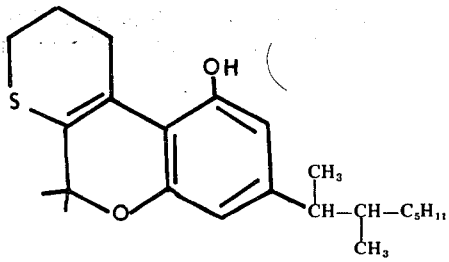

The analgesic activity of the compound useful in the practice of this invention has been demonstrated in mice.

The analgesic activity of the compound was evaluated in an acetic acid writhing test. The acetic acid writhing test used was modified from that described by Whittle, Brit J. Pharmacol., 22, 296 (1964). The number of writhes were counted for a 20 minute period beginning 5 minutes after the injection of the acid. Analgetic potency was calculated from the difference between the test groups and their controls. The analgesic activity of compound I in the acetic acid writhing test is summarized in the following Table 1:

Table 1

| Acetic acid writhing test in mice (oral) | |
|---|---|
| Dose mg/kg p.o. | Percent inhibition |
| 5 | 20.7 |
| 10 | 48.9 |
| 20 | 74.0 |
| 40 | 95.6 |

Compound I was shown by the acetic acid writhing test to have an oral $ED_{50}$ value of 10.8 mg/kg (95% C.L. = 9.2 − 12.4).

In the rat tail flick test for analgesic activity [D'Amour and Smith, J. Pharmacol. Exper. Therap. 72, 74 (1941)] compound I exhibited an oral $ED_{50}$ value of 2.7 mg/kg (95% C.L. = 0.9 − 4.8).

In the practice of this invention, compound I can be administered to a mammalian patient in a dosage of about 0.01 to 40 mg./kg. of body weight daily, preferably in divided dosages, i.e., three to four times daily. The compound exhibits analgesic activity when administered by the oral route and the parenteral, i.e., intravenous, intramuscular or intraperitoneal, route. The oral route is the preferred route of administration.

Although compound I can be administered in pure undiluted form, it is advisable to first combine it with a suitable pharmaceutical carrier or adjuvant to attain a more satisfactory size to dosage relationship.

Solid pharmaceutical carriers such as calcium carbonate, starch, sugar, talc and the like may be used to form powders. The powders may be used as such or be tableted or be used to fill capsules. Suitable lubricants like magnesium stearate, binders such as gelatin and disintegrating agents like sodium carbonate in combination with citric acid may be used to form the tablets. Care in the choice of solid carriers and other ingredients should be exercised to avoid reaction of the active agent with the excipients.

Unit-dosage forms such as tablets and capsules may contain any suitable predetermined amount of compound I as the active agent and can be administered one or more at a time at regular intervals. Such forms should generally contain a minimum concentration of 0.1% by weight of active agent, and particularly 1 to 75 mg., and desirably 1 to 20 mg., of active agent.

A typical tablet can be prepared from a mixture of 89.0 g. of mannitol, 4.0 g. of Carbopol-934 (a binder disclosed in U.S. Pat. No. 2,909,462), 16.5 g. of compound I, and 2.5 g. of stearic acid. The mixture is blended by passage through a No. 20 screen and slugged in the usual way on a tablet slugging machine. The slugs are ground through a No. 20 screen and compressed into tablets using a ¼ inch punch and die. This formulation is for 1000 tablets. Each tablet is to contain 16.5 mg. of compound I.

The compound can also be formulated for administration in liquid form and used for intramuscular injection. Still further, the compound can be formulated for oral administration in aqueous alcohol, glycol or oil solutions or oil-water emulsions in the same manner as conventional medicinal substances are prepared.

The following example is presented to illustrate a chemical method of making compound I.

EXAMPLE 1

1,2-Dihydro-5,5-dimethyl-10-hydroxy-8-(3-methyl-2-octyl)-3H,5H-thiopyrano[2,3-c][1]benzopyran A. Methyl 3-oxo-2,3,4,5-tetrahydro-6H-thiopyran-2-carboxylate The procedure of Leonard and Figueras (J. Amer. Chem. Soc. 74, 917 (1952)) was followed for the cyclization of 20 g. of carbomethoxymethyl γ-carbomethoxypropyl sulfide to give 11.1 g. (70%) of methyl 3-oxo-2,3,4,5-tetrahydro-6H-thiopyran-2-carboxylate. The structure was confirmed by IR and NMR spectra.

B. 1,2-Dihydro-10-hydroxy-8-(3-methyl-2-octyl)-5-oxo-3H,5H-thiopyrano[2,3-c][1]benzopyran A solution of 14.2 g. (0.06 mole) of 5-(3-methyl-2-octyl)resorcinol and 11.1 g. (0.063 mole) of methyl 3-oxo-2,3,4,5-tetrahydro-6H-thiopyran-2-carboxylate in 90 ml. of absolute ethanol was cooled in an ice-salt bath and saturated with anhydrous hydrogen chloride. After standing for 2 days at room temperature, the ethanol was removed on a rotary evaporator. The residue was dissolved in ether, washed with sodium bicarbonate solution and dried over sodium sulfate. Evaporation of the solvent gave 28.0 g. of residue which was chromatographed using activated magnesium silicate (60–100 mesh) and graded methanol/chloroform solvent mixtures. A total of 10 g. of crude solid was obtained from the 1% methanol/chloroform fractions. The material was recrystallized twice from ethyl acetate/hexane to give 8.5 g. (40%) colorless crystals, m.p. 131°–133°C. The proposed structure was confirmed by IR and NMR spectra.

C. 1,2-Dihydro-5,5-dimethyl-10-hydroxy-8-(3-methyl-2-octyl)-3H,5H-thiopyrano[2,3-c][1]benzopyran Methylmagnesium bromide was prepared by bubbling bromomethane into a mixture of 7.68 g. (0.32 mole) of magnesium turnings in ether. When all the magnesium had reacted, the solution was refluxed for a short time to remove the excess bromomethane. A solution of 6.96 g. (0.02 mole) of the pyrone (prepared as above) in benzene was added and the reaction mixture was kept at 45°C for 24 hours. The reaction mixture was decomposed with saturated ammonium chloride; the organic layer was separated and the aqueous layer was extracted twice with ether. The organic layers were combined, washed with water, dried and evaporated to give a gummy residue. The IR and NMR spectra indicated the compound to be 5-(3-methyl-2-octyl)-2-[4,5-dihydro-2-(2-hydroxy-2-propyl)-6H-thiopyran-3-yl]]resorcinol.

A small quantity of p-toluenesulfonic acid was added to a benzene solution of the above triol and the mixture was heated at reflux for 1½ hours in the presence of nitrogen. The benzene solution was washed with sodium bicarbonate solution, dried over sodium sulfate and evaporated to give a greenish-brown residue.

Chromatography using activated magnesium silicate (60–100 mesh) and graded ether/petroleum ether solvent mixtures gave 5.2 g. (60%) of a nearly colorless gum. The gum exhibited $\lambda_{max}^{EtOH}$ 305 m$\mu$ (log$\epsilon$ 4.262) and the IR, NMR and UV spectra confirmed the structure as 1,2-dihydro-5,5-dimethyl-10-hydroxy-8-(3-methyl-2-octyl)-3H,5H-thiopyrano [2,3-c][1]benzopyran.

Anal. Calcd. for $C_{23}H_{34}O_2S$: C, 73.73; H, 9.15; S, 8.54 Found: C, 73.55; H, 9.12; S, 8.45

The foregoing detailed description has been given for clearness of understanding only, and no unnecessary limitations should be understood therefrom, as modifications will be obvious to those skilled in the art.

What is claimed is:

1. A method of relieving pain in a mammalian patient suffering therefrom comprising administering to said patient a therapeutically effective amount of 1,2-dihydro-5,5-dimethyl-10-hydroxy-8-(3-methyl-2-octyl)-3H,5H-thiopyrano[2,3-c][1]benzopyran.

2. The method of claim 1 in which the named compound is administered in a dosage of from about 0.01 to 40 mg/kg daily.

* * * * *